(12) United States Patent
Shaw et al.

(10) Patent No.: US 6,677,294 B2
(45) Date of Patent: Jan. 13, 2004

(54) CLEANSING COMPOSITIONS

(75) Inventors: Gretchen Linnea Shaw, Philadelphia, PA (US); Nicola Jacqueline Phipps, Bracknell (GB); Edward Dewey Smith, III, Mason, OH (US); Frank Neumann, Cincinnati, OH (US); James Anthony Staudigel, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 99 days.

(21) Appl. No.: 09/725,649

(22) Filed: Nov. 29, 2000

(65) Prior Publication Data

US 2002/0107156 A1 Aug. 8, 2002

(51) Int. Cl.⁷ .............................................. C11D 17/00
(52) U.S. Cl. .................. 510/438; 510/439; 510/424; 510/426; 510/428; 510/499; 424/443
(58) Field of Search ................. 510/438, 439, 510/424, 499, 426, 428; 424/443

(56) References Cited

U.S. PATENT DOCUMENTS

| | | | |
|---|---|---|---|
| 2,438,091 A | 3/1948 | Lynch | 260/482 |
| 2,658,072 A | 11/1953 | Kosmin | 260/513 |
| 3,928,251 A | 12/1975 | Bolich, Jr. et al. | 252/545 |
| 3,929,678 A | 12/1975 | Laughlin et al. | 252/526 |
| 4,342,314 A | 8/1982 | Radel et al. | 128/287 |
| 4,343,726 A | 8/1982 | Egan et al. | 252/547 |
| 4,447,294 A | 5/1984 | Osborn, III | 162/158 |
| 4,673,525 A | 6/1987 | Small et al. | 252/132 |
| 4,814,109 A | 3/1989 | Wittpenn, Jr. et al. | 252/547 |
| 5,000,868 A | 3/1991 | Wittpenn, Jr. et al. | 252/106 |
| 5,139,705 A | 8/1992 | Wittpenn, Jr. et al. | 252/547 |
| 5,487,884 A | 1/1996 | Bissett et al. | 424/59 |
| 5,518,801 A | 5/1996 | Chappell et al. | 428/152 |
| 5,565,421 A | 10/1996 | Aszman et al. | |
| 5,716,922 A | 2/1998 | Curry et al. | |
| 6,284,259 B1 * | 9/2001 | Beerse et al. | 424/404 |
| 6,391,835 B1 * | 5/2002 | Gott et al. | 510/143 |
| 2001/0018068 A1 | 8/2001 | Lorenzi et al. | |

FOREIGN PATENT DOCUMENTS

| | | |
|---|---|---|
| EP | 1 010 422 A2 | 6/2000 |
| GB | 809060 | 2/1959 |
| GB | 2 187 750 A | 9/1987 |
| WO | WO 91/16034 | 10/1991 |
| WO | WO 91/16035 | 10/1991 |

* cited by examiner

*Primary Examiner*—Necholus Ogden
(74) *Attorney, Agent, or Firm*—Eileen L. Hughett; Ian S. Robinson; Ken K. Patel

(57) ABSTRACT

Disclosed are cleansing compositions comprising one or more surfactants selected from the group consisting of: i) anionic surfactants, ii) amphoteric surfactants, iii) nonionic surfactants, iv) cationic surfactants and v) mixtures thereof, where the dynamic viscosity of the compositions at 25° C. is at least about 100,000 centipoise and where the cleansing composition results in no or minimal eye sting. Also disclosed disposable articles comprising water insoluble substrates releasably containing the cleansing compositions, a process for making the disposable articles and a method of use.

11 Claims, 5 Drawing Sheets

CLEANSING COMPOSITIONS

TECHNICAL FIELD

The present invention relates to cleansing compositions comprising one or more surfactants selected from the group consisting of: i) anionic surfactants, ii) amphoteric surfactants, iii) nonionic surfactants, iv) cationic surfactants and v) mixtures thereof, where the dynamic viscosity of the compositions at 25° C. is at least about 100,000 centipoise and where the cleansing composition results in no or minimal eye sting.

The instant cleansing compositions are preferably used in releaseable combination with a disposable substrate as a personal cleansing product.

BACKGROUND OF THE INVENTION

Personal care products, particularly cleansing and conditioning products, have traditionally been marketed in a variety of forms such as bar soaps, creams, lotions, and gels. Typically, these products must satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair overly dry after frequent use. Further, cleansing compositions, particularly shampoos, designed for use with children should exhibit mildness to the ocular mucosae, and no or minimal eye sting, should material from the cleansing composition be placed in the eye.

U.S. Pat. No. 5,139,705 (Wittpenn, Jr., et al.) discloses mild non-irritating surfactant compositions which include an anionic surfactant, an amine oxide, a nonionic surfactant having a relatively low melting point and a nonionic surfactant having a high melting point relative to the low melting point nonionic surfactant. The compositions of Wittpenn, Jr., et al. contain approximately 90% water. The viscosity requirements of the products of the instant invention would not be met by Wittpenn's compositions.

It is highly desirable to deliver cleansing and conditioning benefits from a disposable substrate. Disposable products are convenient because they obviate the need to carry or store cumbersome bottles, bars, jars, tubes, and other forms of clutter associated with cleansing products and other products capable of providing therapeutic or aesthetic benefits. Disposable products are also a more sanitary alternative to the use of a sponge, washcloth, or other cleansing implement intended for extensive reuse, because such implements can develop bacterial growth, unpleasant odors, and other undesirable characteristics related to repeated use.

There is also a need for personal care articles, such as disposable washcloths, which can be easily used by young children. Such child-friendly personal care products must be easy to handle and the method of utilizing them must be easily understood. In addition to mildness to the ocular mucosae, there should be no or minimal eye sting, should material from the cleansing composition contact the eye while a child is using the article. Therefore, the invention encompasses disposable cleansing articles wherein the cleansing composition produces no or minimal eye sting when introduced into the eye.

Disposable substrates containing mild cleansing compositions producing no or minimal eye sting, would also facilitate such tasks as make-up removal (particularly eye make-up) and cleaning of animals, such as pets.

While a variety of cleansing compositions associated with substrates are known in the art, they are not appropriate for use where substantial amounts of cleansing composition can be deposited into the eye. The present invention overcomes these problems by providing a cleansing composition which generates no or minimal eye sting.

SUMMARY OF THE INVENTION

The present invention relates to cleansing compositions in paste form comprising one or more surfactants selected from the group consisting of: i) anionic surfactants, ii) amphoteric surfactants, iii) nonionic surfactants, iv) cationic surfactants, and v) mixtures thereof, where the viscosity of the compositions at 25° C. is at least about 100,000 centipoise and where the cleansing composition results in no or minimal eye sting.

One embodiment of the cleansing composition has a first dynamic viscosity at 25° C. and a second dynamic viscosity over a temperature range of 60° C. to 125° C., said first and second dynamic viscosities having a ratio of said first dynamic viscosity to said second dynamic viscosity greater than or equal to about 1.1.

In addition embodiments of the cleansing composition have a first flow viscosity at 25° C. and a second dynamic viscosity over a temperature range of 60° C. to 125° C., said first and second flow viscosities having a ratio of said first flow viscosity to said second flow viscosity greater than or equal to about 1.1.

Compositions exhibiting these preferred ratios of viscosities are extremely viscous at room temperature (25° C.) but become liquid at relatively low temperatures, allowing for ease in processing while contributing to stability on the substrate, i.e., the instant cleansing compositions tend to remain on the substrate due to their viscosity at room temperature. Cleansing compositions with the above characteristics are considered "hot melt" surfactant compositions.

BRIEF DESCRIPTION OF THE DRAWINGS

FIG. 1B is a perspective view of FIG. 1a.

FIG. 3A is a top plan view of a circular pad of insoluble substrate with a grid of cleansing composition printed on.

FIG. 3B is a perspective view of the circular pad of FIG. 3a.

FIG. 5B is a perspective view of the article of FIG. 5a.

FIG. 6B is a perspective view of the article of FIG. 6a.

DEFINITIONS

Figure 1A:
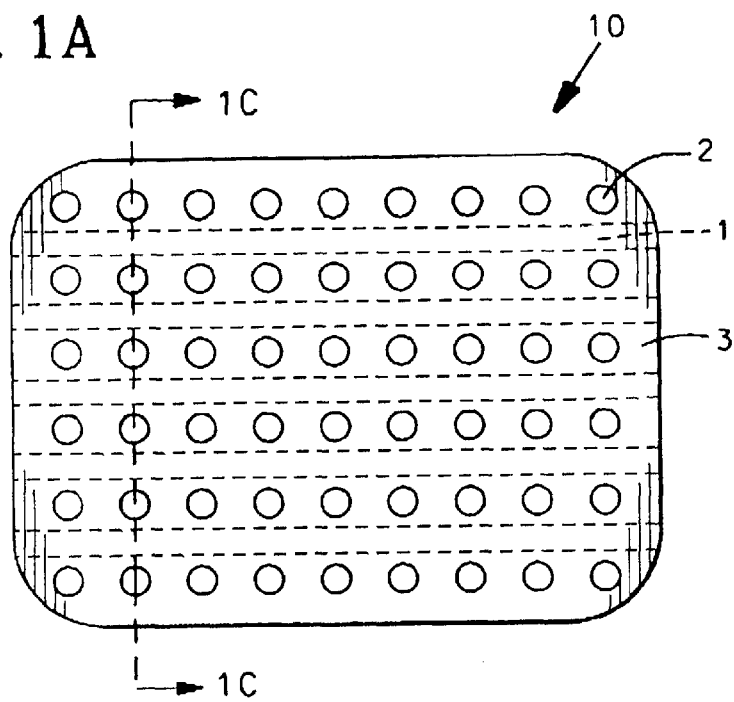
FIG. 1A is a plan view of a preferred embodiment of the present invention with stripes of cleansing composition and circular bonding points.

All percentages and ratios used herein, unless otherwise indicated, are by weight and all measurements made are at 25° C., unless otherwise designated. The invention can comprise, consist of, or consist essentially of, the essential as well as optional ingredients and compositions described herein.

As used herein the abbreviation "gsm" means "grams per square meter".

As used herein the abbreviation "cps" means "centipoise per second".

All documents referred to herein, including patents, patent applications, and printed publications, are hereby incorporated by reference in their entirety in this disclosure.

As used herein, "disposable" is used in its ordinary sense to mean an article that is disposed or discarded after a limited number of usage events, preferably less than 25, more preferably less than about 10, and most preferably less than about 2 entire usage events.

As used herein, "substantially dry" means that the articles of the present invention exhibit a Moisture Retention Value of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The determination of the Moisture Retention Value is discussed hereinafter.

As used herein "paste" or "paste form" means a composition of semisolid consistency.

Also, as used herein, "non-scouring" means having an Abrasiveness Value of greater than about 15, preferably greater than about 30, more preferably greater than about 50, even more preferably greater than about 70, and most preferably greater than about 80, as defined by the Abrasiveness Value Methodology described below.

DETAILED DESCRIPTION OF THE INVENTION

The present invention comprises a cleansing composition which comprises a specific surfactant system as described above. The present invention also comprises a cleansing article with comprises said cleansing composition releasably disposed on a water insoluble substrate.

In another preferred embodiment of the composition, the anionic surfactant is preferably an alkyl ether sulfate. In an even more preferable embodiment, this alkyl ether sulfate is sodium laureth sulfate. In an additional preferred embodiment of the composition, the amphoteric surfactant is a betaine. In an even more preferable embodiment, this betaine is cocoamidopropyl betaine. In yet another preferred embodiment of the composition, the nonionic surfactant is PEG 200 glyceryl tallowate.

An advantage of this invention is that the instant articles are suitable for use by young children in personal cleansing. Due to the ease and simple method of use and the fact that usage of the instant the cleansing composition results in low or no eye sting, very young children are able to bathe themselves, to an extent independently, with the instant articles.

Examples of additional uses of the instant cleansing compositions in combination with disposable substrates are washcloths for make up removal, specifically eye make up removal and cloths for cleaning animals, particularly pets.

A. CLEANSING COMPOSITION

The cleansing composition comprises one or more surfactants selected from the group consisting of: i) anionic surfactants, ii) amphoteric surfactants, iii) nonionic surfactants, iv) cationic surfactants, and v) mixtures thereof, wherein the dynamic viscosity of the composition meets specific viscosity specifications outlined above and wherein the cleansing component results in no or minimal eye sting.

The surfactants of the cleansing component may be lathering or non-lathering surfactants. As used herein, "lathering surfactant" means a surfactant, which when combined with water and mechanically agitated generates a foam or lather. A "nonlathering surfactant" produces no such foam or lather under similar conditions. It is preferred, however, that the surfactants be lathering since increased lather is important to consumers as an indication of cleansing effectiveness.

The surfactants or combinations of surfactants should be mild. As used herein, "mild" means that the surfactants as well as the articles of the present invention demonstrate skin mildness comparable to a mild alkyl glyceryl ether sulfonate (AGS) surfactant based synthetic bar, i.e., synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H$—$H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to those skilled in the art can also be used.

A wide variety of lathering surfactants are useful herein and include those selected from the group consisting of anionic lathering surfactants, nonionic lathering surfactants, amphoteric lathering surfactants, and mixtures thereof.

Anionic Lathering Surfactants

Nonlimiting examples of anionic lathering surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975, each of which is incorporated by reference herein in their entirety.

A wide variety of anionic surfactants are potentially useful herein. Nonlimiting examples of anionic lathering surfactants include those selected from the group consisting of alkyl sulfates and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonates, alkyl glyceryl sulfonates, alkyl glyceryl esters, alkyl glycinates, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, amid ether sulfates, and combinations thereof. Combinations of anionic surfactants can be used effectively in the present invention.

Preferred anionic surfactants for use in the cleansing component include alkyl and alkyl ether sulfates. These materials have the respective formulae $R^1O\text{—}SO_3M$ and $R^1(CH_2H_4O)x\text{—}O\text{—}SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine (TEA), diethanolamine (DEA) and monoethanolamine (MEA). The alkyl sulfates are typically made by the sulfation product of monohydric alcohols (having from about 8 to about 24 carbon atoms) using sulfur trioxide or other known sulfation techniques. The alkyl ether sulfates are typically made by sulfation of condensation products of ethylene oxide and monohydric alcohols (having from about 8 to about 24 carbon atoms). These alcohols can be derived from fats, e.g., coconut oil or tallow, or can be synthetic. Specific examples of alkyl sulfates which may be used in the cleansing component are sodium, ammonium, potassium, magnesium, and TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO\text{—}O\text{—}CH_2\text{—}C(OH)H\text{—}CH_2\text{—}O\text{—}SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^1SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium C14/C16 alpha olefin sulfonate.

Other suitable anionic surfactants are the linear alkylbenzene sulfonates of the form $R^1\text{—}C_6H_4\text{—}SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing component include the primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium C13–C17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate as detailed in U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing component is the acyl isethionates. The acyl isethionates typically have the formula $R^1CO\text{—}O\text{—}CH_2CH_2SO_3M$ wherein $R^1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1\text{—}OCH_2\text{—}C(OH)H\text{—}CH_2SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R^1\text{—}CH(SO_4)\text{—}COOH$ and sulfonated methyl esters of the form $R^1\text{—}CH(SO_4)\text{—}CO\text{—}O\text{—}CH_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These can also be formed by other known phosphation methods. An example from this class of surfactants is sodium mono or dilaurylphosphate.

Other anionic materials include acyl glutamates corresponding to the formula $R^1CO\text{—}N(COOH)\text{—}CH_2CH_2\text{—}CO_2M$ wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula $R^1$—$(OCH_2CH_2)x$—$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate. Other anionic materials include acyl lactylates corresponding to the formula $R^1CO$—$[O$—$CH(CH_3)$—$CO]x$—$CO_2M$ wherein $R^1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Other anionic materials include natural soaps derived from the saponification of vegetable and/or animal fats & oils exmaples of which include sodium laurate, sodium myristate, TEA palmitate, potassium stearate, sodium tallowate, and sodium cocoate.

Any counter cation, M, can be used on the anionic surfactant. Preferably, the counter cation is selected from the group consisting of sodium, potassium, ammonium, monoethanolamine, diethanolamine, and triethanolamine. More preferably, the counter cation is ammonium.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty alcohols, alkoxylated fatty acid esters, sucrose esters, and mixtures thereof.

Alkyl glucosides and alkyl polyglucosides are useful herein, and can be broadly defined as condensation products of long chain alcohols, e.g., about $C_{8-30}$ alcohols, with sugars or starches or sugar or starch polymers, i.e., glycosides or polyglycosides. These compounds can be represented by the formula $(Su)_n$—$O$—$R$ wherein Su is a sugar moiety such as glucose, fructose, mannose, and galactose; n is an integer of from about 1 to about 1000, and R is an about $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein Su is a glucose moiety, R is an about C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

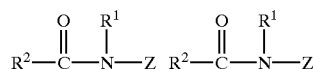

wherein: $R^1$ is H, $C_1$–$C_4$ alkyl, 2-hydroxyethyl, 2-hydroxypropyl, preferably about $C_1$–$C_4$ alkyl, more preferably methyl or ethyl, most preferably methyl; $R^2$ is $C_5$–$C_{31}$ alkyl or alkenyl, preferably about $C_7$–$C_{19}$ alkyl or alkenyl, more preferably about $C_9$–$C_{17}$ alkyl or alkenyl, most preferably about $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$—moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; each of which are incorporated herein by reference in their entirety.

Other examples of nonionic surfactants include amine oxides. Amine oxides correspond to the general formula $R1R_2R_3N{\rightarrow}O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected from the group consisting of about $C_8$–$C_{14}$ glucose amides, about $C_8$–$C_{14}$ alkyl polyglucosides, sucrose cocoate, sucrose laurate, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates alkylammonium propionates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

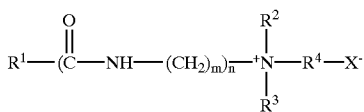

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds: Cetyl dimethyl betaine (this material also has the CTFA designation cetyl betaine)

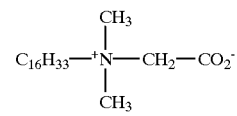

Cocamidopropylbetaine

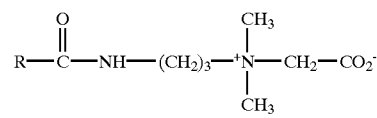

wherein R has from about 9 to about 13 carbon atoms
Cocamidopropyl hydroxy sultaine

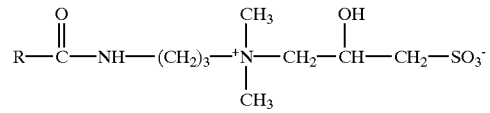

wherein R has from about 9 to about 13 carbon atoms,
Examples of other useful amphoteric surfactants are alkyliminoacetates, and iminodialkanoates and aminoalkanoates of the formulas $RN[(CH_2)_mCO_2M]_2$ and $RNH(CH_2)_mCO_2M$ wherein m is from about 1 to 4, R is An about $C_8$–$C_{22}$ alkyl or alkenyl, and M is H, alkali metal, alkaline earth metal ammonium, or an alkanolammonium. Also included are imidazolinium and ammonium derivatives. Specific examples of suitable amphoteric surfactants include sodium 3-dodecyl-aminopropionate, sodium 3-dodecylamino-propane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants are selected from the group consisting of anionic lathering surfactants selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phospate, sodium cocoglyceryl ether sulfonate, sodium $C_9$–$C_{22}$ soap, and combinations thereof; nonionic lathering surfactants selected from the group consisting of lauramine oxide, cocoamine oxide, decyl polyglucose, lauryl polyglucose, sucrose cocoate, $C_{12\text{-}14}$ glucosamides, sucrose laurate, and combinations thereof; cationic lathering surfactants selected from the group consisting of fatty amines, di-fatty quaternary amines, tri-fatty quaternary amines, imidazolinium quaternary amines, and combinations thereof; amphoteric lathering surfactants selected from the group consisting of disodium lauroamphodiacetate, sodium lauroamphoacetate, cetyl dimethyl betaine, cocoamidopropyl betaine, cocoamidopropyl hydroxy sultaine, and combinations thereof.

Cationic Lathering Surfactants

Cationic lathering surfactants are also useful in the articles of the present invention. Suitable cationic lathering surfactants include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate. The fatty amines, however, are preferred. It is preferred that a lather booster is used when the cationic lathering surfactant is the primary lathering surfactant of the cleansing component. Additionally, nonionic surfactants have been found to be particularly useful in combination with such cationic lathering surfactants.

B. VISCOSITY/TEMPERATURE RELATIONSHIP OF CLEANSING COMPOSITIONS

As disclosed above, the cleansing compositions of the instant invention are, preferably, "hot melt" surfactant systems. Hot melt surfactant systems have high viscosity at or around room temperature, and then melt (become substantially liquid) at higher temperatures. Such systems are advantageous during processing of a disposable, substantially dry (or dry to the touch) cleansing article since the surfactant system can be applied (e.g., coated, sprayed, extruded) to the substrate at a low viscosity (e.g., a liquid) at higher than room temperature, and then as the system cools down, it becomes a high viscosity paste or solid. In the present invention there is a required range of temperatures and viscosities at which these changes take place.

Unless otherwise noted, all viscosities are measured as dynamic viscosities, as described herein.

Another consideration is stability of the finished product. The cleansing composition must maintain a certain viscosity at or around room temperature (25° C.) so that when the product is stored, the system stays stable on the substrate (and does not melt off). This lower viscosity limit is at least 100,000 centipoise for the present invention. The viscosity at higher temperatures is preferably less than 100 million centipoise in order to keep the system easy to process.

There is also a temperature range at which the cleansing composition undergoes significant changes in viscosity. The instant cleansing compositions are highly viscous at room temperature and melt into liquid form at a temperature below 125° C. The temperature at which the composition melts should not be too low in order to prevent the cleansing composition, which has been deposited on the substrate from becoming unstable (i.e., likely to melt) during normal usage conditions (room temperature up to −25° C.), but should not be too high or the temperature necessary in order to apply the cleansing composition to the substrate will degrade the surfactants and any perfume that may be present (>125° C.). Therefore, for the present invention, it is preferred that the significant viscosity change occurs at a temperature within the range of about 25° C. to about 125° C., preferably within the range of about 40° C. to about 70° C., and most preferably within the range of about 40° C. to about 60° C.

Due to these constraints, there is a requirement of the aforementioned significant viscosity change that the ratio of the dynamic viscosities of the cleansing composition are such that the cleansing composition has a first dynamic viscosity at 25° C. and a second dynamic viscosity over a temperature range of 60 to 125° C., the first and second dynamic viscosities having a ratio of the first dynamic viscosity to the second dynamic viscosity of greater than or equal to 1.1, more preferably greater than or equal to 5, even more preferably greater than or equal to 8, and most preferably, greater than or equal to 10. This requirement ensures that the viscosity change is significant enough to allow a process advantage.

Additionally, the flow viscosities preferably have a similar ratio at the same temperatures.

C. WATER INSOLUBLE SUBSTRATE/ARTICLE

In a preferred embodiment, the present invention is an article comprising a water insoluble substrate with the cleansing composition described above deposited thereon. The water insoluble substrate comprises at least one layer, a substrate sheet to which the instant paste form cleansing composition is applied. In a preferred embodiment there is at least an additional substrate sheet which is joined to the substrate sheet to which the paste has been applied and which overlays the cleansing composition.

The Figures illustrate preferred embodiments of the present invention.

Top plan view FIG. 1A shows stripes 1 of cleansing composition (location only, not visible in actual article), bonding sites 2 multiple, and second substrate sheet 3, which comprises a finished article (10).

Figure 1B:
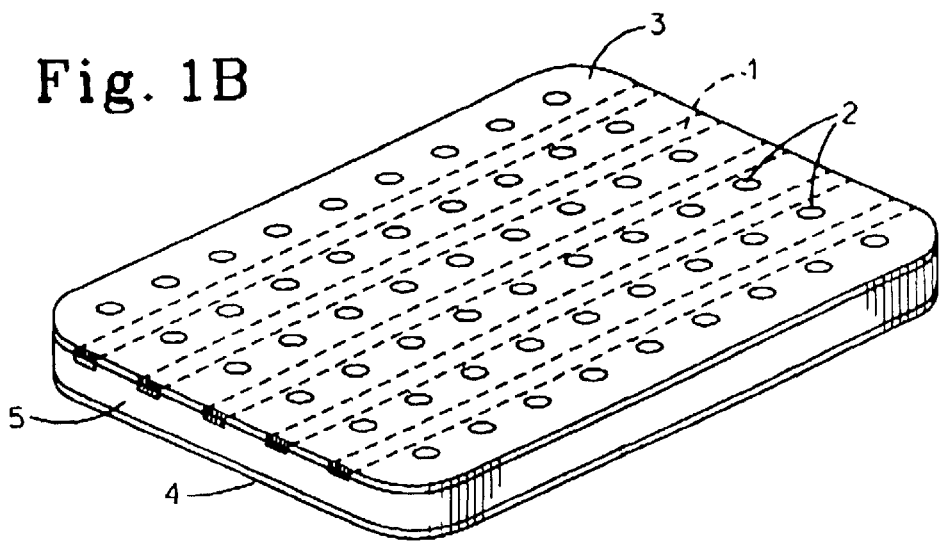

Perspective view FIG. 1B (of the embodiment shown in FIG. 1A) shows first substrate sheet 5 with stripes 1 of cleansing composition thereon and covered with second substrate sheet 3, third substrate sheet 4, and bonded at sites 2 multiple.

Figure 1C:
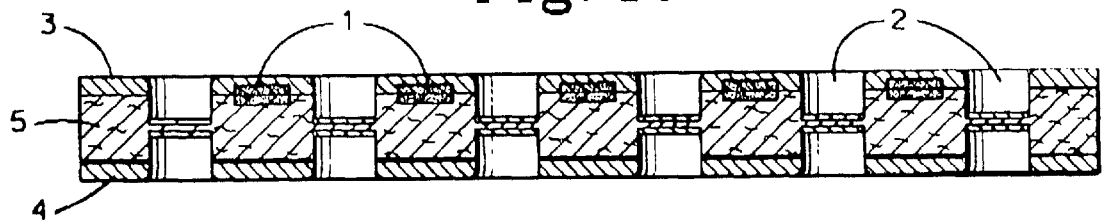
FIG. 1C is a cross sectional view of FIG. 1A taken along Line 1C.

FIG. 1C is a cross sectional view, taken along line 1C of FIG. 1A, showing first substrate sheet 5, bonding sites 2, second substrate sheet 3, with stripes of cleansing composition 1 deposited thereon and third substrate sheet 4.

Figure 2A:
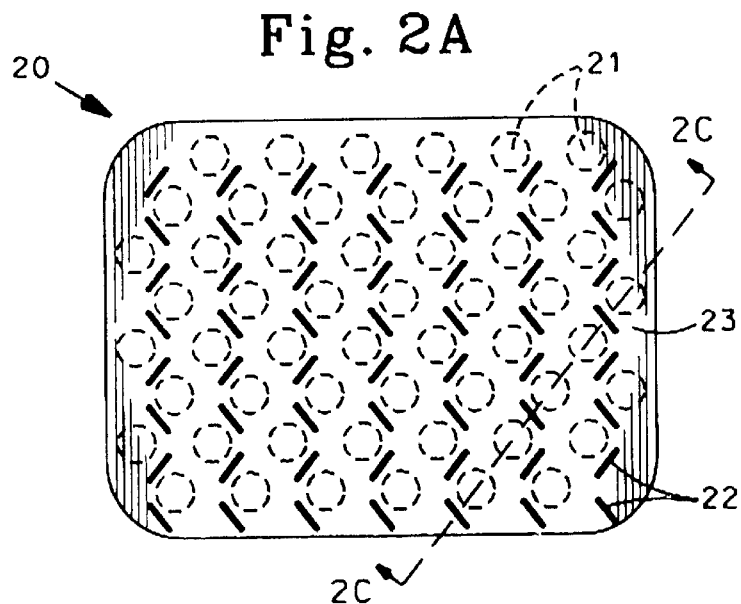
FIG. 2A is a plan view of a preferred embodiment of the present invention with dots of cleansing composition and short bonding lines.

Top plan view FIG. 2A shows the location of dots of cleansing composition 21 (indicated on second substrate sheet 23 in dashed lines as the deposit of the dots is not actually visible in the top plan view), bonded at sites multiple 22 which comprises a finished article (20).

Figure 2B:
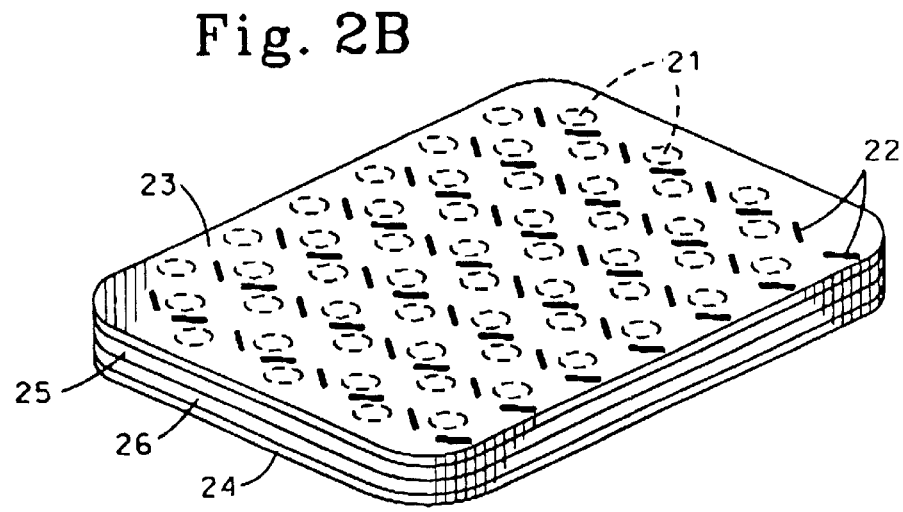
FIG. 2B is an expanded perspective view of FIG. 2a, showing a cross section and illustrating the structure of the article.

Perspective view FIG. 2B taken along line 2C of FIG. 2A, shows the location of dots of cleansing composition 21 (indicated on second substrate sheet 23 in dashed lines as the deposit of the dots is not actually visible in the top plan view), bonded at sites multiple 22, third substrate sheet 24, first substrate sheet 25, and fourth substrate sheet 26 which comprises a finished article.

Figure 2C:
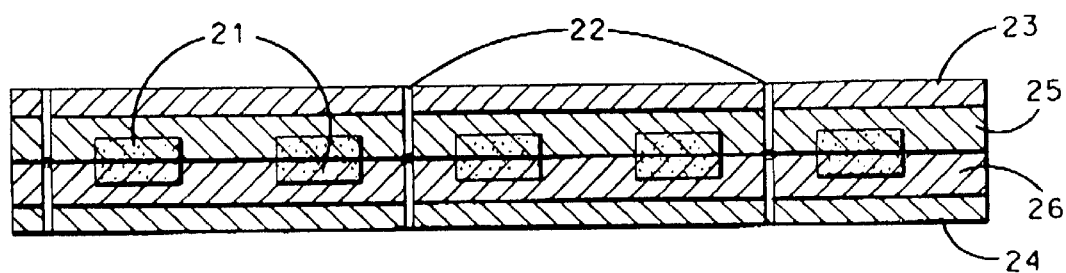
FIG. 2C is a cross sectional view of FIG. 2A taken along Line 2C.

Cross sectional view FIG. 2C taken along line 2C of FIG. 2A, shows dots of cleansing composition 21, bonded at sites multiple 22, second substrate sheet 23, third substrate sheet 24, first substrate sheet 25, and fourth substrate sheet 26.

Figure 3A:
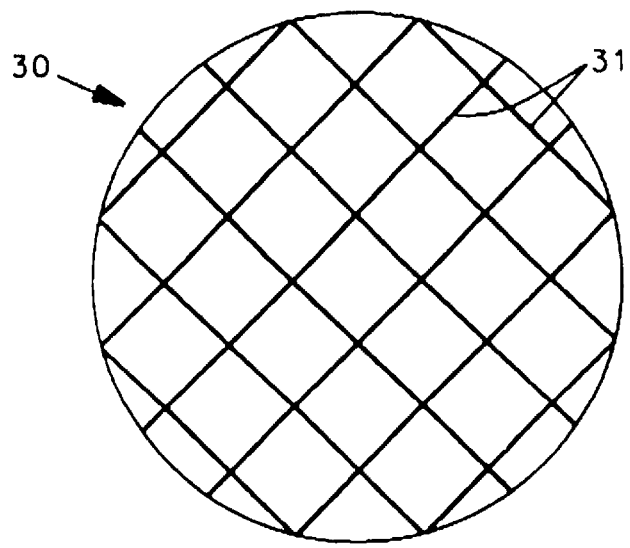

Top plan view FIG. 3A shows lines 31 of cleansing composition deposited in the form of a grid onto a substrate sheet 32 which comprises a finished article (30).

Figure 3B:
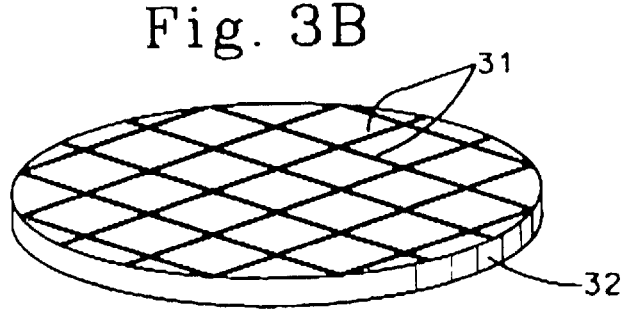

Perspective view FIG. 3B of the embodiment of FIG. 3A, shows lines 31 of cleansing composition deposited in the form of a grid onto a substrate sheet 32.

Figure 4:
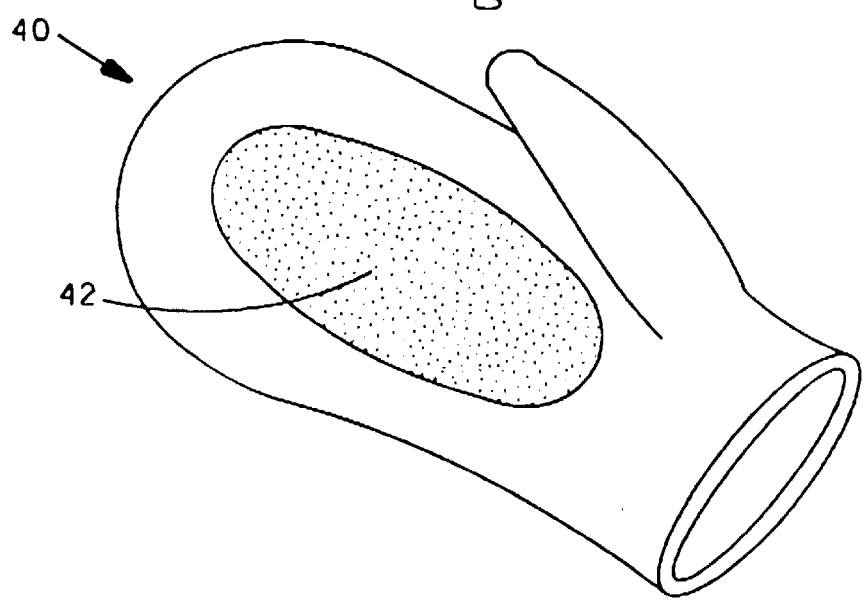
FIG. 4 is a perspective view of a mitt with cleansing composition applied in the center of the palm.

FIG. 4 shows an article in the form of a mitt of substrate sheet 42 with cleansing composition 1 deposited in the area of the palm which comprises a finished article (40).

Figure 5A:
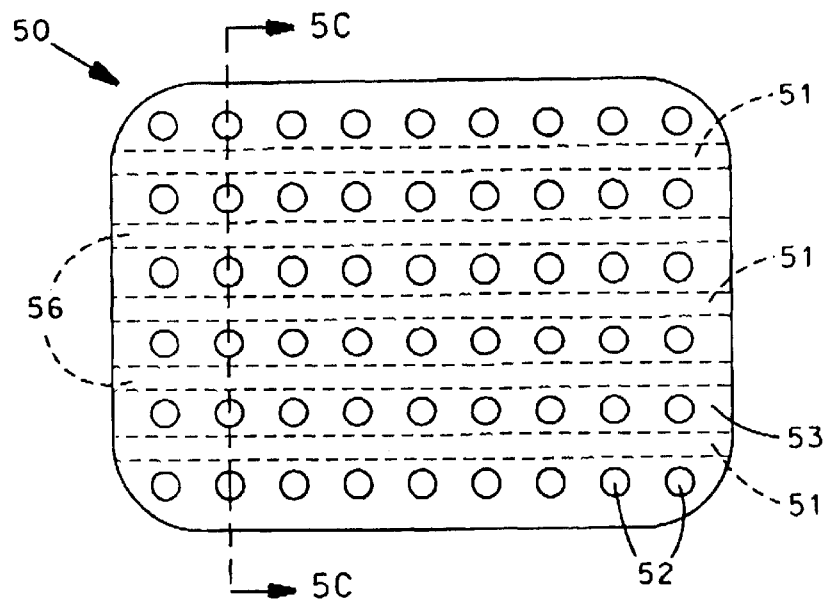
FIG. 5A is a top plan view showing alternative positions of the cleansing component in relation to a benefit agent in a multiple chambered embodiment of the article of the present invention.

Top plan view FIG. 5A shows stripes 51 of cleansing composition, stripes 56 of benefit agent (neither of these stripes is visible in the actual article as they are deposited onto the middle layer), bonding sites 52 multiple and second substrate sheet 53 which comprises a finished article (50).

Figure 5B:
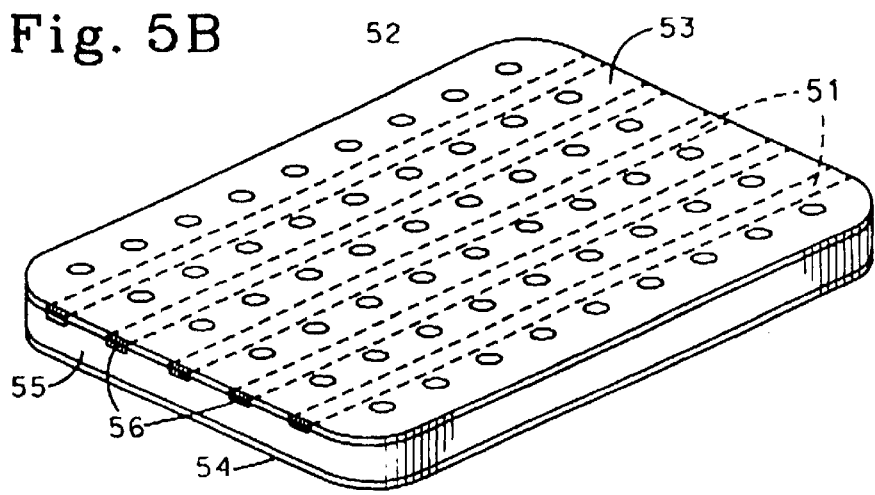

Perspective view FIG. 5B of the embodiment of FIG. 5A, shows second substrate sheet 53 and first substrate sheet 55 with stripes 51 of cleansing composition and stripes of benefit agent 56 therein, bonding sites 52 multiple, and third substrate sheet 54.

Figure 5C:
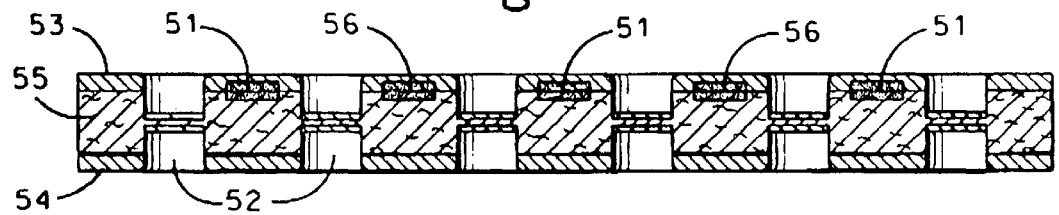
FIG. 5C is a cross sectional view of FIG. 5A taken along Line 5C.

Cross sectional view FIG. 5C taken along line 5C of of FIG. 5A, shows stripes 51 of cleansing composition, stripes 56 of benefit agent, bonding sites, multiple 52, second substrate sheet 53, third substrate sheet 54, first substrate sheet 55.

Figure 6A:
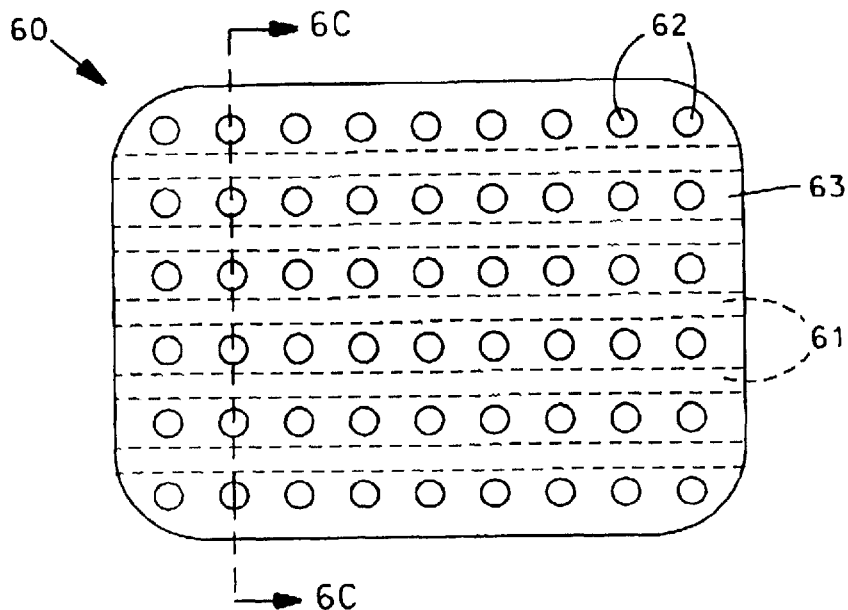
FIG. 6A is a top plan view showing alternative positions of the cleansing component in relation to a benefit agent in a multiple chambered embodiment of the article of the present invention.

Top plan view FIG. 6A shows stripes (61) of cleansing composition, bonding sites, multiple (62) with embedded benefit agent and second substrate sheet (63) which comprises a finished article (60).

Figure 6B:
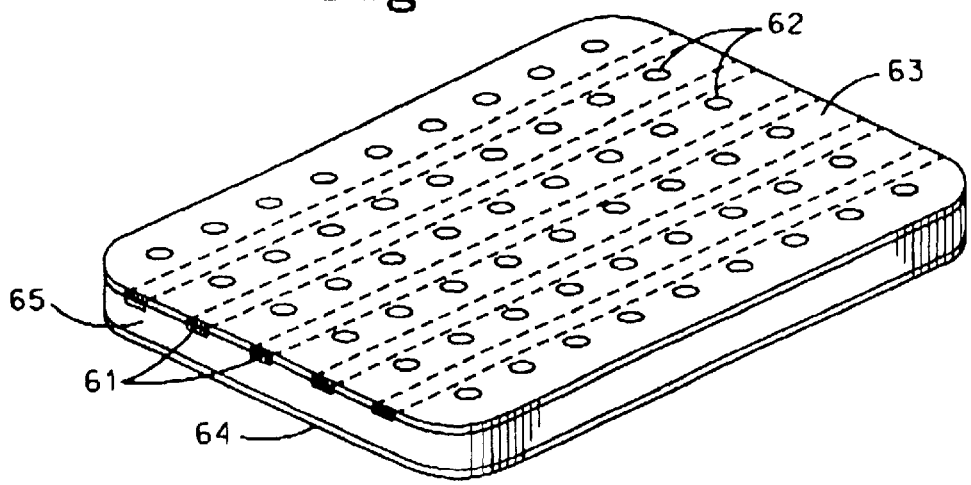

Perspective view FIG. 6B of the embodiment of FIG. 6A, shows first substrate sheet (65) with stripes (61) of cleansing composition thereon, second substrate sheet (63), third substrate sheet (64), and bonded at sites (62), multiple with embedded benefit agent.

Figure 6C:
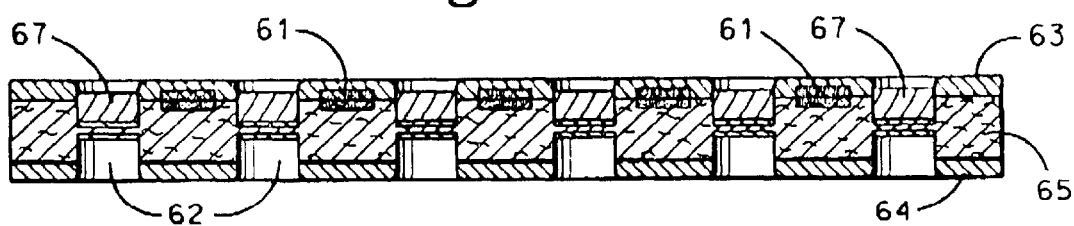
FIG. 6C is a cross sectional view of FIG. 6A taken along Line 6C.

Cross sectional view FIG. 6C taken along line 6C of FIG. 6A, shows stripes of cleansing composition (61), bonded at sites (62), multiple, first substrate sheet (65), second substrate sheet (63), third substrate sheet (64), and benefit agent embedded at bonding sites (67) which comprises a finished article (60).

When the cleansing composition is disposed on the water insoluble substrate, the articles of the present invention comprise from about 0.5% to about 3,000%, preferably from about 50% to about 2,000%, and more preferably from about 100% to about 1,500%, based on the weight of the untreated water insoluble substrate, of the surfactant composition. Also, for personal cleansing purposes a preferred article of the present invention preferably comprises at least about 1 gram, by weight of the treated water insoluble substrate, of a surfactant.

Preferably, the substrate sheets are soft to the skin of the consumer when used. In any case, however, the first sheet and the second sheet are each defined as having both an interior and an exterior surface. In both cases, the interior surfaces of the sheets are those which face the inside or innermost portion of the article of the present invention whereas the exterior surfaces of the sheets are those which face the outside or outermost portion of the article.

In yet another preferred embodiment, the article of the present invention comprises one or more additional substrate sheets which one having ordinary skill in the art would recognize as separate and distinct from the first and second sheets yet which are attached to the first and second sheets at some point. The additional sheets are suitable for enhancing the overall grippability of the side of the article closest to the hand or other means for exerting mechanical action on the surface to be cleansed. Also, the additional sheets may be suitable for enhancing either the soft feel or scrubbing efficacy of the side of the article which contacts the area to be cleansed. In any instance, these additional sheets may also be referred to as consecutively numbered sheets in addition to the two essential sheets of the articles of the present invention, e.g., third sheet, fourth sheet, etc.

In a preferred embodiment, at least one additional sheet is positioned adjacently to the exterior surface of the first sheet such that it forms the outermost portion of the article. In this capacity, the third sheet is useful for providing a surface suitable for facilitated gripping of the article by the hand. It is therefore desirable that when the additional sheet is positioned adjacently to the exterior surface of the first sheet, the third sheet exhibits a higher wet friction coefficient relative to the other sheets of the article.

In another embodiment, the article comprises a fourth sheet which is disposed adjacent to the second sheet wherein the fourth sheet comprises the same as or different materials from the third sheet.

Suitable materials for use as sheets of the water insoluble substrate are selected from the group consisting of, but not limited to, nonwovens, wovens, sponges, polymeric netted meshes, formed films, battings, and combinations thereof. In preferred embodiments, the additional sheets may be composite materials such that they each consist of one or more plies, each ply being made from the same or different materials than the other plies.

In a preferred embodiment, the additional sheets of the articles of the present invention have a thickness of at least one millimeter. In this preferred embodiment, the additional sheets having a thickness of at least one millimeter provide structural support for the article such that its original shape is maintained throughout its useful life and the sheet also tends to enhance the softness perception to the consumer.

Materials suitable for use as the sheets of the water insoluble substrate having a thickness of at least one millimeter include, but are not limited to, those web materials disclosed in U.S. Pat. No. 5,518,801, issued to Chappell et al. on May 21, 1996, which is incorporated by reference herein in its entirety.

Additional materials that are suitable for use as the sheets of the water insoluble substrate of the present invention include the cellulosic nonwovens described in U.S. Pat. No. 4,447,294, the formed films of U.S. Pat. Nos. 4,342,314 and 4,629,643.

Furthermore, each of the sheets of the water insoluble substrate of the present invention may be made into a wide variety of shapes and forms including flat pads, thick pads, thin sheets, ball-shaped implements, irregularly shaped implements. The exact size of the sheets will depend upon the desired use and characteristics of the article and may range in surface area size from about a square inch to about hundreds of square inches. Especially convenient layer and article shapes include, but are not limited to, square, circular, rectangular, hourglass, or oval shapes having a surface area of from about 5 $in^2$ to about 200 $in^2$, preferably from about 6 $in^2$ to about 120 $in^2$, and more preferably from about 15 $in^2$ to about 100 $in^2$, and a thickness of from about 0.5 mm to about 50 mm, preferably from about 1 mm to about 25 mm, and more preferably from about 2 mm to about 20 mm.

D. OPTIONAL COMPONENTS

The cleansing compositions and/or articles of the present invention may contain a variety of other components such as are conventionally used in a given product type provided that they do not unacceptably alter the benefits of the invention. These optional components should be suitable for application to human skin and hair; that is, when incorporated into the article they are suitable for use in contact with human skin without undue toxicity, incompatibility, instability, allergic response, and the like, within the scope of sound medical or formulator's judgment.

The *CTFA Cosmetic Ingredient Handbook*, Second Edition (1992) describes a wide variety of nonlimiting cosmetic and pharmaceutical ingredients commonly used in the skin care industry, which are suitable for use in the articles of the present invention. Examples of these ingredient classes include: enzymes, absorbents, aesthetic components such as fragrances, pigments, colorings/colorants, essential oils, skin sensates, anti-acne agents (e.g., resorcinol, sulfur, salicylic acid, erythromycin, zinc, etc.), anti-caking agents, antifoaming agents, additional antimicrobial agents (e.g., quaternium-15, methyl paraben, ethyl paraben, propyl paraben, DMDM hydantoin etc.), antioxidants, binders, biological additives, buffering agents, bulking agents, chelating agents, chemical additives, colorants, cosmetic biocides, denaturants, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, hydrocolloids, particular zeolites, and vitamins and derivatives thereof (e.g., tocopherol, tocopherol acetate, beta carotene, retinoic acid, retinol, retinoids, retinyl palmitate, niacin, niacinamide, and the like). The cleansing compositions and/or articles of the present invention may include carrier components such as are known in the art. Such carriers can include one or more compatible liquid or solid filler diluents or vehicles which are suitable for application to skin or hair. Typically, such material can be incorporated into the cleansing compositions and comprise from about 0.01% to about 40%, by weight, of the compositions herein. Additionally, the optional components can be applied to the substrate sheet as a deposit separate from that of the cleansing composition.

The cleansing compositions and/or articles of the present invention may optionally contain one or more of such optional components.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Chelators

The cleansing compositions of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage. Typically, such materials can comprise from about 0.01% to about 40%, by weight, of the compositions herein.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication Ser. No. 91/16035, Bush et al., published Oct. 31, 1995; and International Publication Ser. No. 91/16034, Bush et al., published Oct. 31, 1995. Preferred chelators useful in compositions of the subject invention are furildioxime and derivatives thereof.

Binders

The cleansing compositions of the present invention may optionally comprise binders. Binders or binding materials are useful for sealing the various layers of the present articles to one another thereby maintaining the integrity of the article. The binders may be in a variety of forms including, but not limited to, spray on, webs, separate layers, binding fibers, etc. Suitable binders may comprise latexes, polyamides, polyesters, polyolefins and combinations thereof. Typically, such materials comprise from about 0.01% to 40% of the compositions herein.

E. PROPERTIES OF ARTICLE COMPONENTS

The articles of the present invention exhibit specific physical properties as defined by the both the Dynamic and Flow Viscosity Measurement, Eye Sting Test, Abrasiveness Value Test, Foamability Test and the Moisture Retention Value Methodology. These methods are described below.

Dynamic Viscosity Measurement

Dynamic viscosity of the compositions is measured using a viscometer (available from TA Instruments of New Castle, Del. as model number AR-1000N) in an oscillation mode. The measurements are conducted using a parallel plate measuring system, having a diameter of 40 mm and a gap of 600 micron. The measurement commences after about 180 seconds equilibration time. Measurements are conducted on a temperature sweep from about 20° C. to 80° C. The dynamic viscosity measured at 2.498 Hz frequency and 0.50 Pa oscillatory stress is used to characterize the compositions. That is, all the dynamic viscosities disclosed and/or claimed herein are measured at the operating conditions given above.

Flow Viscosity Measurement

The flow properties of the composition are measured using a viscometer (available from TA Instruments of New Castle, Del. as model number AR-1000N) in a flow mode. The measurements are conducted using a parallel plate measuring system, having a diameter of 40 mm and a gap of 600 micron. The measurement commences after about 180 seconds equilibration time. Viscosity measurements are conducted on a continuous shear ramp at both 25° C. and 60° C. with a shear rate of 10 inverse seconds (1/s).

Eye Sting Test

Twenty (20) panelists are given four (4) articles comprising the cleansing composition of Example 1 (below) deposited onto a water insoluble substrate. They are instructed to wash their faces with each of the articles using the lathered article directly on or near the eye area. They are then asked to fill out a questionnaire detailing how they used the articles and if there was any irritation (eye or skin) caused by the article. The compositions of the present invention exhibit no to minimal eye sting when used on or near the facial area. For instance, "mild irritation" would be considered equivalent to no or minimal eye sting pursuant to this test.

Abrasiveness Value Methodology

The Abrasiveness Value indicates the "non-scouring" property of the water insoluble substrate layers of the present articles. The layers of the present invention can be mildly exfoliating but are not rough (i.e., are soft) to the skin. Therefore, the Abrasiveness Value determination involves rubbing the substrate along a test surface using a mechanical device and then examining the resulting scratch marks produced on the test surface using different analysis techniques.

The following equipment is needed for the methodology.
1. Martindale Toothbrush Wear and Abrasion Tester: Model 103, serial nos. 103–1386/2 upwards. Martindale 07-01-88 made by James H. Heal and Co. Ltd. Textile Testing and QC Equipment. Foot area: 43×44 mm. 1 Kg weight.
2. Capped Polystyrene strips 11×8 cm. Clear general purpose polystyrene layer on white High Impact Polystyrene eg. EMA Model Supplies SS-20201L.

3. Substrates to be tested.

4. Glossmeter e.g. Sheen Tri-Microgloss 20-60-85

Prepare the polystyrene strips for scratching by removing plastic protective coating from the side to be scratched and rinsing with ethanol (do not use tissue). Place the strip onto non abrasive surface and allow strip to dry in the air. Then, attach the polystyrene strip to the base of a Martindale wear tester with tape along the edges. Align the strip centrally under the path of the scrubbing device, with the length of the strip in the direction of movement. Cut a 2.5"×2.5" substrate sample. Attach the substrate sample to the scrubbing foot of the Martindale wear tester, with double sided tape, aligning the machine direction of the substrate with the direction of travel. Secure the scrubbing foot assembly into the instrument with the screws supplied. Slot 1 Kg weight on to the top of the scrubbing foot assembly and ensure the scrubbing foot moves only in one direction (forward and backwards). Cover the entire Martindale wear tester with a safety screen. Set the machine to perform 50 cycles in 1 minute and allow to run. (Frequency=0.833 Hz). Once the machine has stopped take off the footer assembly and lift the polystyrene strip off the base of the machine. Label the polystyrene indicating the substrate used and store in a plastic bag.

Next, the strips are analyzed. The strips are placed on a black construction paper background and at least 5 samples of the same substrate are analyzed to get a reproducible average. The Glossmeter is placed orthogonally (such that light beam is at right angles to scratches) and centrally over the scratched side of the polystyrene strip. A 20° angle is selected and the sample is measured yielding the Abrasiveness Value. As the Abrasiveness Value decreases the scratchiness or scouring property of a substrate increases.

Moisture Retention Value Methodology

As described above, the articles of the present invention are considered to be "substantially dry". As used herein, "substantially dry" means that the articles of the present invention exhibit a Moisture Retention Value of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The Moisture Retention Value is indicative of the dry feel that users perceive upon touching the articles of the present invention as opposed to the feel of "wet" wipes.

In order to determine the Moisture Retention Value of the present articles and other disposable substrate-based products, the following equipment and materials are needed.

| Bounty White Paper Towel | Procter & Gamble SKU 37000 63037 Basis Weight = 42.14 gsm |
|---|---|
| Balance | Accurate to 0.0 g |
| Lexan | 0.5" thickness large enough to cover samples completely and weighs 1000 g |
| Weight | A 2000 g weight or combination to equal 2000 g |

Next, weigh two paper towels separately and record each weight. Place one paper towel on flat surface (e.g., lab bench). Place the sample article on top of that towel. Place the other paper towel on top of sample article. Next, place the Lexan and then the 2000 g weight(s) on top of the sandwiched sample article. Wait 1 minute. After the minute, remove weight(s) and Lexan. Weigh the top and bottom paper towel and record the weight.

Calculate the Moisture Retention Value by subtracting the initial paper towel weight from the final weight (after 1 minute) for both the top and bottom paper towels. Add the weight differences obtained for the top and bottom paper towels. Assuming multiple articles are tested, average the total weight differences to obtain the Moisture Retention Value.

F. METHODS OF MANUFACTURE

The cleansing articles of the present invention are manufactured by first producing the cleansing composition (paste) by addition of the components and mixing. The cleansing composition is then added to the appropriate water insoluble substrate of the first layer via a conventional method which may include, but is not limited to, spraying, slot coating, and roll transfer (e.g., pressure roll). Where appropriate, the water insoluble substrate of the second layer is then placed on the substrate of the first layer over the cleansing composition.

When two or more of these substrate layers are bonded together any suitable means which one having ordinary skill in the art would choose and be used. Examples are, but are not limited to, heat bonding, ultrasonic bonding, pressure bonding, entangling by water or mechanical means (needling), sewing, gluing (see binders below), etc.

In a preferred embodiment, the bonding sites are created in areas of the article where there is no surfactant or benefit agent present at the bond site for optimal bond strength. Suitable bonding patterns are for example, but are not limited to, bonding in dots, stripes, lines, waves, or even more complex geometries.

G. METHODS OF CLEANSING AND DELIVERING AN OPTIONAL INGREDIENT TO THE SKIN OR HAIR

The articles of the present invention are intended to be wetted with water prior to use. The article is wetted by immersion in water or by placing it under a stream of water. When the articles of the present invention comprise a lathering surfactant in the cleansing composition, lather may be generated from the article by mechanically agitating and/or deforming the article either prior to or during contact of the article with the skin or hair. The resulting lather is useful for cleansing the skin or hair. During the cleansing process and subsequent rinsing with water, any optional ingredients (e.g., therapeutic or aesthetic benefit agents) are deposited onto the skin or hair. Deposition of any such optional ingredients are enhanced by the physical contact of the substrate with the skin or hair as well by the inclusion of one or more deposition aids.

The following examples further illustrate the invention, but are not intended to be limiting.

EXAMPLE I (CLEANSING COMPOSITION)

| Component | % wt. |
|---|---|
| Sodium Laureth-3 Sulfate | 63.6 |
| Cocamidopropyl Betaine | 23.8 |
| PEG-200 Glyceryl Tallowate | 10.0 |
| Polyquaternium-10 | 1.1 |
| Preservative System | 0.5 |
| Whitener | 0.5 |
| Perfume | 0.5 |

Results of Eye Sting Testing of articles comprising a water insoluble substrate and the cleansing composition of Example 1: Five (5) of the twenty (20) panelists experience some sort of eye irritation. Four (4) of these judged the irritation to be "mild" and the irritation occurred with only one of the four articles. Three (3) of these five (5) panelists call the irritation nothing more than a "mild sensation" like that of having water in the eyes. The fifth person experiences moderate irritation, like a particle is lodged in the corner of the eye, and again this occurs with only one of the four articles.

EXAMPLE II (CLEANSING COMPOSITION)

| Component | % wt. |
|---|---|
| Sodium Lauryl Sarcosinate | 49.4 |
| Cocamidopropyl Betaine | 28.0 |
| PEG-200 Glyceryl Tallowate | 20.0 |
| Polyquaternium-10 | 1.1 |
| Preservative System | 0.5 |
| Whitener | 0.5 |
| Perfume | 0.5 |

EXAMPLE III

| | |
|---|---|
| Sodium Laureth-3 Sulfate | 43.6 |
| Cocamidopropyl Betaine | 23.8 |
| Sodium Lauroyl EDTA | 20.0 |
| PEG-200 Glyceryl Tallowate | 10.0 |
| Polyquaternium-10 | 1.1 |
| Preservative System | 0.5 |
| Whitener | 0.5 |
| Perfume | 0.5 |

EXAMPLE IV

A representative skin cleansing article is prepared in the following manner.

The cleansing composition of Example 1 is applied to one side of a first substrate by extruding it through a coating head continuously in four lines separated by a distance of 20 mm, 40 mm, and 20 mm respectively, measuring widthwise across the sheet, making a pair of parallel lines on the face of the interior side of the sheet.

The cleansing composition is extruded at a rate to yield 2.0 grams of cleansing composition per finished article. The substrate sheet is a an airlaid, lofty, low density batting. The batting comprises a blend of 30% 15 denier PET fibers, 35% 3 denier bicomponent fibers with PET core and PE sheath, and 35% 10 denier bicomponent fibers of the same core-sheath composition, and has a basis weight of about 100 grams per square meter (gsm). A second sheet which is a spunlace blend of 50% polyethylene and 50% polypropylene fibers and which has a basis weight of about 30 gsm is continuously fed over the first substrate placing it in contact with the surfactant-containing layer. A third sheet which is a spunlace blend of 50% polyethylene and 50% polypropylene fibers and which has a basis weight of about 30 gsm is continuously fed below the first substrate, thereby, placing it in contact with the bottom of the cleansing composition-containing layer. The sheet are continuously fed to an ultrasonic sealer which seals a dot pattern comprising a grid of 4 mm diameter sealing points spaced evenly across the face of the sheet. The sheet is cut into individual articles measuring about 120 mm×160 mm rectangles with rounded corners, which has a total of about 51 sealing points per article.

The foregoing discloses various examples and embodiments of the invention, but other embodiments fall within the scope of the invention, as would be clear to one of skill in the art.

What is claimed is:

1. A substantially dry disposable personal care article suitable for cleansing, said article comprising:
    a) a soft, non-scouring water insoluble substrate, said substrate releasably containing;
    b) a cleansing composition comprising a blend of an amphoteric surfactant and one or more surfactants selected from the group consisting of:
        i) anionic surfactants,
        ii) nonionic surfactants,
        iii) cationic surfactants, and
        iv) mixtures thereof;
    and wherein the dynamic viscosity of the cleansing composition at a temperature of 25° C. is at least about 100,000 centipoise, the cleansing composition results in no or minimal eye sting, and said substantially dry disposable personal care article is a mitt.

2. The article of claim 1 wherein the cleansing composition has a first dynamic viscosity at 25° C. and a second dynamic viscosity over a temperature range of 60° C. to 125° C., said first and second dynamic viscosities having a ratio of said first dynamic viscosity to said second dynamic viscosity greater than or equal to about 1.1.

3. The article of claim 1 wherein the cleansing composition has a first flow viscosity at 25° C. and a second flow viscosity over a temperature range of 60° C. to 125° C., said first and second flow viscosities having a ratio of said first flow viscosity to said second flow viscosity greater than or equal to about 1.1.

4. The article of claim 1 wherein the anionic surfactant is an alkyl ether sulfate.

5. The article of claim 4 wherein the alkyl ether sulfate is sodium laureth sulfate.

6. The article of claim 1 wherein the betaine is cocoamidopropyl betaine.

7. The article of claim 1 wherein the nonionic surfactant is PEG 200 glyceryl tallowate.

8. A process for producing the substantially dry disposable article of claim 1, said process comprising the steps of:
    a) providing a first water insoluble substrate layer, having an interior surface;
    b) forming a paste containing surface by extruding and distributing onto said interior surface a paste comprising a blend of an amphoteric surfactant and one or more surfactants selected from the group consisting of:
        i) anionic surfactants,
        ii) nonionic surfactants,
        iii) cationic surfactants, and
        iv) mixtures thereof;
    and wherein the dynamic viscosity of the cleansing composition at a temperature of 25° C. is at least about 100,000 centipoise and wherein the cleansing composition results in no or minimal eye sting.

9. The process according to claim 8 further comprising the step of applying at least a second additional water insoluble substrate layer to the paste containing surface of the first water insoluble substrate layer.

10. The process of claim 8 wherein the paste is extruded and or distributed in the form of a pattern.

11. A method of cleansing skin or hair with the disposable cleansing article of claim 1, comprising;
    a) wetting the cleansing article with water, and
    b) contacting the skin or hair with the article, with agitation.

* * * * *